United States Patent
Doyle et al.

[11] Patent Number: 6,080,551
[45] Date of Patent: *Jun. 27, 2000

[54] RAPID ASSAYS FOR THE ASSESSMENT OF ORGAN STATUS BASED ON THE DETECTION OF ONE OR MORE ISOENZYMES OF GLUTATHIONE S-TRANSFERASE

[75] Inventors: John Martin Doyle, Deansgrange; Cormac Gerard Kilty, Sandycove, both of Ireland

[73] Assignee: Biotrin Intellectual Properties, Ltd., Dublin, Ireland

[*] Notice: This patent issued on a continued prosecution application filed under 37 CFR 1.53(d), and is subject to the twenty year patent term provisions of 35 U.S.C. 154(a)(2).

[21] Appl. No.: 08/930,511
[22] PCT Filed: Apr. 2, 1996
[86] PCT No.: PCT/IE96/00019
§ 371 Date: Oct. 3, 1997
§ 102(e) Date: Oct. 3, 1997
[87] PCT Pub. No.: WO96/31779
PCT Pub. Date: Oct. 10, 1996

[30] Foreign Application Priority Data

Apr. 3, 1995 [WO] WIPO ............... PCT/IE95/00024

[51] Int. Cl.[7] ............... G01N 33/573; C12Q 1/48
[52] U.S. Cl. ............... 435/7.4; 435/15
[58] Field of Search ............... 435/7.1, 7.4, 7.92, 435/7.94, 15, 7.5, 7.6, 7.72, 7.9, 7.91, 7.95

[56] References Cited

U.S. PATENT DOCUMENTS 5,217,868  6/1993  Kilty et al. ............... 435/7.4
5,427,917  6/1995  Hosada et al. ............... 435/7.4

FOREIGN PATENT DOCUMENTS 0560410     9/1993   European Pat. Off. .
291194B1    2/1994   European Pat. Off. .
WO 9012088  10/1990  WIPO .
WO 9322452  11/1993  WIPO .
9631779     10/1996  WIPO .

OTHER PUBLICATIONS

Hara et al. J. Cancer Res. Clin Oncol 119: 493–496, 1993.
Trull et al. Transplantation 58(12): 1345–1351, 1994.
Trull et al., Transplantation (1994) 58, 1345–1351.
Beckett and Hayes, Advances in Clinical Chemistry (1993) 30, p. 281–380.
Tiainen et al., Clin. Chem. (1996) 42 2, 334–335.
Howie et al., Clinica Chimica Acta (1989) 184, 269–278.
Tiainen and Karhi, Clin. Chem. (1994) 40–2, 184–189.

Primary Examiner—Donna Wortman
Assistant Examiner—Brenda Brumback
Attorney, Agent, or Firm—Birch, Stewart, Kolasch & Birch, LLP

[57] ABSTRACT

The present invention is drawn to a method for the rapid assessment of organ status, including organ damage following immunological or toxicological insult, in a subject based on the detection of one or more isoenzymes of glutathione S-transferase (GST) in diverse biological fluids comprising contacting a particle-labelled anti-GST antibody specific for said isoenzyme with a sample of a biological fluid suspected of containing said isoenzyme, said antibody having a sensitivity sufficient to detect at least a picomolar amount of said isoenzyme, and capturing the particle-labelled antibody-isoenzyme complex on an immobolised capture antibody to generate a visually detectable signal.

14 Claims, 1 Drawing Sheet

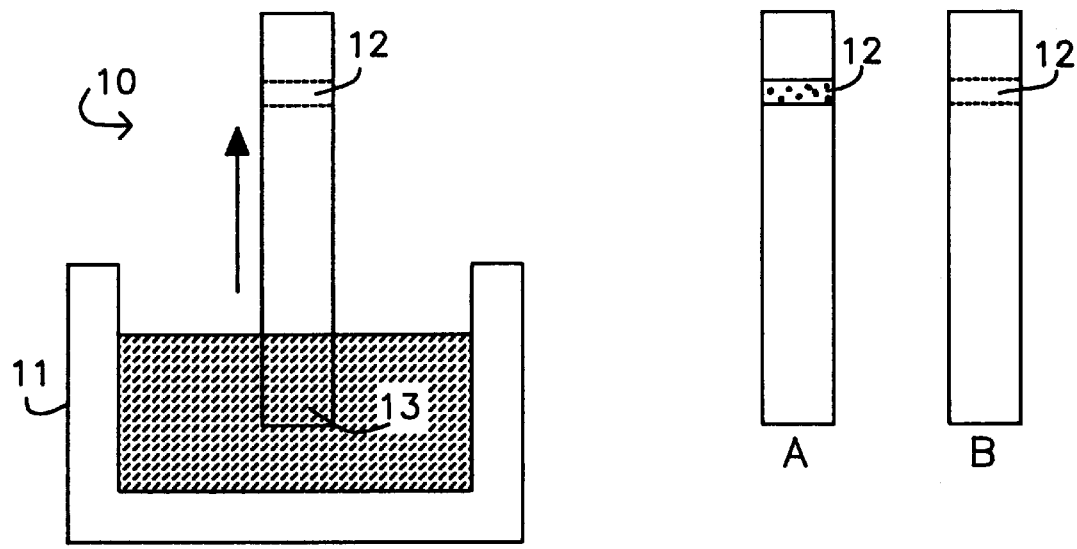
FIG.1A
FIG.1B
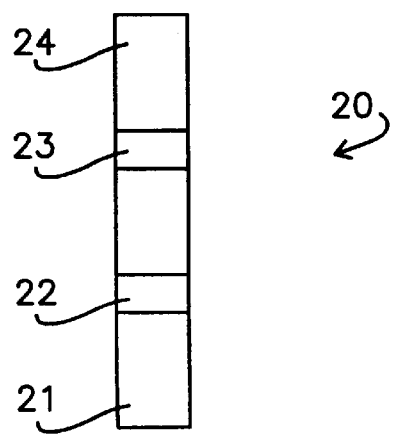
FIG.2

RAPID ASSAYS FOR THE ASSESSMENT OF ORGAN STATUS BASED ON THE DETECTION OF ONE OR MORE ISOENZYMES OF GLUTATHIONE S-TRANSFERASE

TECHNICAL FIELD

This invention relates to a rapid assay format for the detection and/or determination of glutathione S-transferases (GSTs) for use in the assessment of organ status.

BACKGROUND ART

GSTs represent a multigene family of proteins consisting mainly of $\alpha$, $\mu$, $\theta$, and $\pi$-class isoforms and are responsible for the detoxification of a range of xenobiotics, mainly via conjugation to glutathione. Alpha GST ($\alpha$GST) is the major hepatic form and is uniformly distributed throughout the liver. In contrast, PiGST ($\pi$GST) is located mainly in the epithelial cells lining the bile ducts. A similar unique distribution also exists with respect to the renal situation where $\alpha$GST is located in the proximal tubules and $\pi$GST is confined to the distal tubule region of the nephron. It can therefore be concluded that measurement of either plasma or urinary GST levels will facilitate the monitoring of either the hepatic or renal status of an individual. Numerous authors have, indeed, used GST measurements to evaluate both liver and renal damage in individuals who have undergone organ transplant or who have suffered organ damage by virtue of exposure to either hepatic or renal toxins (see, for example, Trull, A. K. et al., Transplantation (1994) 58, 1345–1351).

Currently such measurements are most usually performed using radioimmunoassays (RIA). However, recently a number of microtitre plate-based enzyme immunoassays (EIAs) have become commercially available from Biotrin International Limited, Mount Merrion, County Dublin, Ireland, which allow measurement of $\alpha$ and $\pi$GST levels in biological fluids. These EIAs are now gaining widespread acceptance among the scientific community despite some initial scepticism (c.f. Beckett, G. J. and Hayes, J. D. (Advances in Clinical Chemistry (1993) 30, p.325)). Thus, at present RIA represents the detection method of choice for many workers in the field. Both of these techniques have certain limitations insofar as they require both specialised equipment and highly trained and competent personnel to generate meaningful and accurate results. Such assays are relatively slow requiring on the average 2 hours or more from start to finish. Accordingly, a more rapid assay format for GSTs is required.

Methods for the detection of GST isoenzymes are tending to become increasingly complicated as evidenced by the use of Time-Resolved ImmunoFluorometric Assay (TR-IFMA). Tiainen, P et al. (Clin. Chem. (1996) 42 2, 334–335) compared enzyme immunoassay (EIA) and TR-IFMA for $\alpha$GST. The EIA used was Hepkit (trade mark of Biotrin International, Dublin). It was found that the inter-assay precision was better in Hepkit than in TR-IFMA. Also TR-IFMA is stated to have been somewhat more laborious than Heptkit because more replicates (four) and more washing cycles were needed to complete the assay procedure. Thus, it is clear that current research in to the detection and quantitation of GST has focussed on the development of more elaborate and complicated detection systems such as TR-IFMA.

Individuals who have undergone organ transplant or who have suffered organ damage by virtue of having been exposed to hepatic or renal toxins must be carefully monitored. This is especially true for individuals who have undergone organ transplant and who undergo a long post-transplant period of therapy with immunosuppressive drugs, in particular cyclosporin. Once such individuals are discharged from hospital they must be continuously monitored, which at present necessitates frequent returns to the relevant hospital unit, so that the requisite GST and other assays can be carried out. Accordingly, it would be most desirable if such persons had a means of self-monitoring which would reduce the number of hospital visits but, more importantly, would give an early indication to the patient and physician that intervention is required, in the event that an above-normal level of a GST is noted.

Thus, a method which would allow a faster and simpler format for GST detection in plasma, urine and other biological fluids, such as bile, would be a distinct advantage as it would allow the physician to monitor either the hepatic or renal status of an affected individual without recourse to time-consuming or expensive hospital-based tests.

Another area where a rapid assay format is required is in assessing organs prior to transplantation or in ex vivo experimentation. Currently, there is no generally acceptable method of donor organ evaluation prior to transplant into the recipient. Consequently it is impossible to accurately predict the final outcome of the transplantation operation as judged by the initial quality of the donor organ. Any method which would contribute to the pre-transplant assessment of the donor organ would greatly aid in the evaluation of the final outcome of the operation and may allow the physician to intervene earlier with post-transplant support therapy to prevent graft loss due to poor quality or host rejection.

As part of normal organ retrieval procedures, the donor organ is equilibrated or perfused with specific reagents (e.g. University of Wisconsin Buffer) once removed from the organ donor. This and other such reagents serve to maintain ex vivo organ integrity at low temperatures (4–10° C.) prior to insertion into the recipient and are also used to equilibrate the stored organ to body temperature (37° C.) prior to surgical reattachment to the recipient. Clearly, the quality of the donor organ will be dependent on many factors such as: donor health; time and temperature of ex vivo storage; handling procedures; and the quality of preservation reagents used. Thus, ex vivo graft injury, as caused by any of the above factors, could be monitored by evaluation of enzyme leakage from the organ.

Rapid assay formats are known. For example, EP 0 291 194 B1 describes and claims an analytical test device and an analytical method using said device which are suitable for use in the home, clinic or doctor's surgery and which are indicated to give an analytical result which is rapid and which requires the minimum degree of skill and involvement from the user. The device is indicated to be particularly suitable as a pregnancy testing device. No specific mention is made of GSTs. The levels of marker hormones in pregnant women, such as human chorionic gonadotropin (HCG) tend to be present in higher concentrations, and thus more readily detected, than the levels of GSTs in patients of the type hereinabove described and for whom elevated levels of GST are critical or, indeed, indicative of potential life threatening clinical events.

The difficulty of using enzyme activity measurements for discrimination between the isoforms of GSTs is well documented (Beckett G. J. and Hayes, J. D. (1993) supra). As indicated above, other investigators have used RIA (Howie, A. F. et al. (Clinica Chimica Acta (1989) 184, 269–278) and TR-IFMA (Tiainen, P and Karhi, K. K. Clin. Chem. (1994) 40-2, 184–189) to detect GSTs. Each of these techniques is a very sensitive technique for the detection of biomolecules. However, each technique requires specialised equipment and skilled personnel. For example, TR-IFMA requires the use of a special time-resolved fluorometer.

It will be appreciated that a technique is required which is suitable for non-experts or in a crisis situation which is rapid and easy to use. Representative of crisis situations would be liver damage or kidney damage post-transplant or potential liver failure due to paracetamol overdose.

DISCLOSURE OF INVENTION

Accordingly, the invention provides a method for the rapid assessment of organ status in a subject based on the detection of one or more isoenzymes of glutathione S-transferase (GST) in diverse biological fluids, which method comprises contacting a particle-labelled anti-GST antibody specific for said isoenzyme with a sample of a biological fluid suspected of containing said isoenzyme, said antibody having a sensitivity sufficient to detect at least a picomolar amount of said isoenzyme, and capturing the particle-labelled antibody-isoenzyme complex on an immobilised capture antibody to generate a visually detectable signal.

By "rapid" herein is meant that the detection or determination of the GST isoenzyme is typically completed in a time of the order of 30 minutes from initial contact with the particle-labelled anti-GST.

By organ status herein is included organ damage following immunological or toxicological insult.

It will be apparent to one skilled in the art that one of the major advantages of the invention lies in its simplicity, such that it can be used by persons with little or no scientific training to monitor their own state of health and/or to provide rapid information in crisis situations of the type hereinabove described.

It will be appreciated that no complicated equipment or detailed laboratory procedures are necessary for assay performance or result evaluation and interpretation. This simplicity of performance and result assessment is significantly at variance with current procedures for GST detection.

Preferably, the GST is αGST, πGST or µGST of hepatic or renal origin.

Most preferably the GST is αGST or πGST of hepatic or renal origin.

A particular requirement of any rapid assay format for GST is an antibody with the requisite affinity for the GST.

In the case of αGST, a polyclonal antibody has been raised with an affinity to detect concentrations of αGST as low as 6.5 ng/ml as hereinafter described, which contributes greatly to the overall sensitivity of the method.

In general, an antibody, which may be monoclonal or polyclonal, with an affinity to detect concentrations of GST isoenzymes as low as 5 ng/ml is preferred for use in accordance with the invention.

The anti-GST antibody bound to the solid phase is suitably polyclonal antibody, more especially polyclonal IgG. However, in certain instances such as in the case of πGST, the solid phase antibody is preferably monoclonal antibody.

Suitably, the anti-GST antibody is bound to a nitrocellulose membrane of known type such as that obtainable from Schleicher and Schuell GmbH of Germany. Such membranes have a natural ability to bind proteins, including immunoglobulins. However, it will be appreciated that a variety of solid supports known per se can be used as the support for the capture antibody. Such supports are referred to herein generally as the solid phase.

Suitably, the nitrocellulose membrane has a pore size in the range 5–10 µm.

Non-specific binding sites on the nitrocellulose membrane are optionally blocked depending on the format of the assay adopted as hereinafter described. Suitably, the blocking of non-specific binding sites can be achieved by treatment with a protein such a bovine serum albumin or milk protein or with a polymer such as polyvinyl-pyrrolidone in a manner known per se.

The solid phase can have a variety of constructions and can include devices of the type covered EP 0 291 194 B1 referred to above, provided that the anti-GST antibody used has the requisite specificity.

By specificity of the anti-GST antibody as used herein is meant the affinity of the antibody for the relevant GST. This affinity is expressed in terms of the concentration of analyte detectable rather than in more theoretical terms, such as in terms of a specific affinity Ka at a given concentration.

The solid phase can be accommodated in a housing of a plastics material and can be provided with a wick at one or both ends to facilitate chromatographic movement of the components of the immunoassay.

The biological fluid used in the method according to the invention is suitably bile, plasma, serum or urine, more especially plasma, serum or urine.

The biological fluid can be diluted or undiluted (neat).

The biological fluid can also be a perfusate and thus the method according to the invention can be used to evaluate an organ prior to transplantation or ex vivo experimentation.

As stated above, no such generally accepted method exists for the evaluation of donor organs. We have shown that rapid GST detection in perfusates is possible using the method according to the invention as a marker of ex vivo organ status. Rapidity of detection is essential in this situation since the donor organ is undergoing unidirectional and constant ex vivo hypoxia which will ultimately lead to irreversible damage thus rendering the organ useless for transplantation. Therefore, any test which would allow organ assessment will be of great benefit to the physician.

The biological fluid is contacted with particle-labelled anti-GST antibody so that the GST isoenzyme to be detected is bound to said particle-labelled anti-GST antibody prior to being contacted with solid phase immobilised antibody. Particles which can be used as labels include colloidal particles, latex particles and metallic sol particles. Metallic sol particles are suitably gold particles having an average diameter in the range 15–40 nm. Such gold particles are commercially available and are marketed, for example, by Janssen Life Sciences Products.

The particle-labelled anti-GST antibody can also be disposed adjacent the sample application end of any device to be contacted with the biological fluid in accordance with the invention.

The use of particle-labelled anti-GST antibody means that no amplification step is involved. Thus, in the case of particle-labelled anti-GST antibody detection of GST isoenzymes, detection can be based simply on direct antibody-antigen interaction using particle-labelled antibodies for antigen detection or interaction visualisation with the attendant advantages in the situations hereinabove described.

This is all the more surprising, given that it will be apparent from the literature that there has been some scepticism in the scientific community even as regards the use of EIAs for GST detection, even though an amplification system is involved which enhances the sensitivity of detection.

The provision of a wick at either end of the solid phase as hereinabove described is particularly preferred when particle-labelled anti-GST IgG is used, since it facilitates chromatographic movement of the labelled IgG. For example, in the case of a nitrocellulose membrane, the provision of a wick at the sample application end and another at the top of the membrane will facilitate chromatographic movement of gold-labelled IgG previously sprayed onto the membrane. Furthermore, the inclusion of purified GST above the immobilised anti-GST IgG on the membrane would act as an internal/procedural control for the gold-labelled anti-GST IgG conjugate function.

In this embodiment, liquid present in a biological sample resuspends the gold-labelled anti-GST IgG and any GST isoenzyme present is bound by the gold-labelled IgG. This complex then migrates up or along the membrane attracted by the upper wick. If sufficient GST isoenzyme is present, then the GST/gold-labelled anti-GST IgG complex is immobilised onto the membrane where bound anti-GST IgG is present. This results in a positive signal indicating that GST is present in the sample. Excess gold-labelled anti-GST IgG conjugate would bind to the procedural control (GST) on the membrane.

It will also be appreciated that when particle-labelled antibody is used to bind antigen in the biological sample, then the determination of bound GST can be carried out in a single step by what can be described as a 'one pot' assay.

The invention also provides a kit for carrying out a method for the detection of GST as hereinbefore defined which contains an anti-GST antibody which is specific for a GST isoenzyme as herein described.

The assay format described herein differs from the aforementioned EIA and RIA type immunoassays in two main respects. Firstly, the order of antigen detection is different insofar as in the method according to the invention the antigen is firstly bound to the particle-labelled antibody (PLA) and then this antigen-PLA complex is captured by the immobilised capture antibody to generate a positive signal. Thus there is no requirement for any intermediate steps such as membrane washing to remove unbound material (e.g, other urinary, blood or perfusate components) or the addition of any amplification reagent to facilitate detection of bound antigen-PLA complex: the complex is, in fact, 'self-detecting'.

This situation contrasts sharply with current methods of GST immunodetection (EIA/RIA) wherein the antigen is firstly contacted with an immobilised capture antibody and after numerous extended washing procedures to remove unbound/interfering components, antibody conjugate (antibody-enzyme or radioactivity labelled antibody) is added to the antigen-antibody complex to detect bound antigen. In the case where antibody-enzyme conjugates are utilised, it is necessary in all cases to add an additional reagent, a substrate, whereby bound enzyme is detected by the appearance of a coloured product.

Both enzyme- and radioimmunoassay methodologies require expensive and complicated equipment to allow the research scientist or laboratory technician to interpret the significance of the experimental data. When a rapid assay format is utilised for GST immunodetection in accordance with the invention the end result is simply indicated by the presence or absence of a colour (band) and is easily interpretable by the non-expert.

The second main area of difference between the method according to the invention and the known assay systems has already been alluded to above and this aspect centres around the lack of requirement for signal amplification to facilitate GST immunodetection in the present assay format. In fact, the sensitivity of detection required for the rapid detection of GST in accordance with the invention is inherent in the assay format. No extraneous amplification reagents are required other than the particle-labelled antibody and the capture antibody. Other techniques for GST immunodetection all utilise some method of signal amplification including enzymatic production of a coloured product (EIA), fluorescence enhancement using $Eu^{3+}$ labelled antibodies (TR-IFMA) and the extensive signal amplification associated with particle emission from the atomic nucleus (i.e, radioactive detection) (RIA).

BRIEF DESCRIPTION OF DRAWINGS

FIG. 1 is a schematic representation of a rapid assay format in accordance with the invention using gold-labelled anti-αGST IgG and membrane bound anti-αGST IgG as described in Examples 2 and 3; and FIG. 2 is a schematic representation of a rapid assay format in accordance with the invention using gold-labelled anti-αGST IgG and membrane bound anti-αGST IgG as described in Example 4.

MODES FOR CARRYING OUT THE INVENTION

The invention will be further illustrated with reference to the accompanying Examples.

EXAMPLE 1

αGST Purification and Antisera Generation using Purified αGST

αGST purification

Human liver was obtained at autopsy. Liver homogenisation was carried out by adding 113.2 g of liver to 400 ml of a homogenisation buffer at pH 7.2 having the following composition:

10 mM sodium phosphate 250 mM sucrose 1 mM EDTA followed by cell disruption for 2 minutes at 4° C. in a Waring (Waring is a trade mark) blender. The resultant homogenate was centrifuged at 11,500 g for 10 minutes after which the supernatant was removed and again centrifuged at 48,000 g for 45 minutes. The final supernatant (380 ml) was dialysed extensively against 20 mM Tris-HCl at pH 7.8 and 4° C. Once dialysis was complete, the dialysate was applied to an S-hexyl GSH Sepharose® affinity column. αGST bound specifically to this column and was eluted using 0.3 mM S-hexyl GSH.

A quality control check was then carried out as follows:

1. αGST so purified was found to be pure by SDS-PAGE.
2. Purified αGST reacted with anti-αGST antisera but not with anti-π or anti-μGST antisera.
3. Isoelectric focussing showed two bands at pI (isoelectric points) 8.5 and 7.8. Purified $B_1$ $B_1$ (αGST) provided one band at pI 8.5. Accordingly, it is postulated that the band with pI 7.8 may be the $B_2$ containing dimer of αGST.

Preparation of antisera to human αGST

The preparation of antisera to human αGST was carried out as follows over the indicated time period using rabbits (internal I.D.: Syncor G and H) using the following protocol.

Day 1:

Carry out a test bleed of 5 ml preserum from the ear of the rabbit then mix 0.5 ml of human αGST antigen (100 µg) with an equal volume of Freund's Complete Adjuvant. Homogenise the antigen and adjuvant to ensure good emulsion. This mixture is then injected subcutaneously into multiple sites on the back of the rabbit which has previously been shaved.

Day 28:

Carry out a test bleed of 5 ml preserum from the ear of the rabbit then mix 0.5 ml of human αGST antigen (100 µg) with an equal volume of Freund's Complete Adjuvant. Homogenise the antigen and adjuvant to ensure good emulsion. This mixture is then injected subcutaneously into multiple sites on the back of the rabbit.

Day 42:

A test bleed of 10 ml of blood is taken from the rabbit's ear.

Day 56:

A second boost is given to the rabbit as described on Day 28.

Day 70:

A test bleed of 10 ml of blood is taken from the ear of the rabbit. When the titre is sufficiently high, the rabbit is sacrificed and as much blood as possible is collected.

Antibody purification:

10 ml antisera (rabbit) is applied to a 10 ml column of Protein A Sepharose previously equilibrated in phosphate buffer saline (PBS). Rabbit IgG (total) binds to the Protein A and is eluted using 0.1 M glycine at pH 3.0. Purity is established by SDS-PAGE and functionality (anti-GST activity) is established by microtitre plate coating, dot blot and Western blot analysis and direct conjugation to horseradish peroxidase (HRP).

In the case of microtitre plate coating, the concentration of anti-αGST used is 1 µg/ml in 0.1 M sodium carbonate buffer at pH 9.6.

The anti-αGST IgG-HRP conjugate concentration for use in an enzyme immunoassay for αGST having an αGST detection range of 0–50 ng/ml was found to be 77 ng/ml. This result indicates the high sensitivity of the antibody, because normally the concentration required for such enzyme immunoassays (for example, the EIA marketed under the trade mark Mukit by Biotrin International Limited, Mount Merrion, County Dublin, Ireland and EIAs of other companies) would be greater than 700–7,000 ng/ml for other rabbit IgG-HRP conjugates.

EXAMPLE 2

αGST Particle-Based Assay

1. Anti-αGST IgG (0.5 mg/ml in PBS) was line-sprayed onto nitrocellulose membrane strips (3 mm×8 cm). No blocking step was included in the membrane preparation.

However the inclusion of such a procedure may aid strip stability and reduce non-specific binding.

2. Anti-αGST antibodies were labelled with gold particles (15 and 40 nm diameter) by a contract manufacturer supplied with the antibody and were stored in 0.1% (w/v) sodium azide in 2 mM sodium tetraborate at pH 7.2 as diluent.

Assay procedure

1. αGST-containig samples were mixed with a given volume of gold-labelled anti-αGST IgG using the following diluent:

1% (w/v) bovine serum albumin

1% (w/v) TWEEN-20 in PBS, pH 7.2 and were tested as hereinafter described.

2. The nitrocellulose membrane, pre-coated with anti-αGST IgG (1–3 mm wide), was dipped into the mixture and left in place for up to 3–5 minutes.

Testing Procedure

The rapid assay procedure was carried out on the following samples (Sample Nos. 1–5):

Sample No 1. αGST at 25 µg/ml (25 mg/l).

Sample No 2. Three diluted urine samples with known αGST concentrations: a) 6.01, b) 18.34 and c) 1.03 ng/ml, respectively—before 1/5 dilution).

Sample No 3. Diluent only.

Sample No 4. πGST.

Sample No 5. αGST at 50 ng/ml (50 µg/L).

Results

Sample No 1. A signal was obtained for the 25 µg/ml solution which indicates that even at levels 1000× greater than normal urinary αGST levels no 'hook effect' (false positive) is observed.

Sample No 2a–2c. αGST present in all three urine samples (diluted 1/5 in dilution buffer) was detected and the signal intensity was proportional to the original αGST concentration as observed by three independent observers.

Sample No 3. No signal was observed when diluent only was tested in the rapid assay format.

Sample No 4. No signal was observed.

Sample No 5. This solution gave a clear detectable signal in the assay.

EXAMPLE 3

αGST Particle-Based Assay

1. Anti-αGST IgG (murine monoclonal; 1 mg/ml in PBS) was immobilised onto nitrocellulose membrane strips (0.5×4 cm)

2. The strips were blocked by incubation for 30 minutes at room temperature in a solution of 2% (w/v) non-fat milk and 2% (w/v) polyvinylpyrrolidone in Tris buffered saline, pH 7.4, containing 0.5% (w/v) Tween 20.

3 The strips were rinsed with distilled water, and dried for 1 hour at room temperature.

4. Anti-αGST antibodies were labelled with gold particles (40 nm diameter) by a contract manufacturer supplied with the antibody, and were stored in 0.1% (w/v) sodium azide in 2 mM sodium tetraborate at pH 7.2 as diluent.

Assay Procedure:

1. αGST containing samples were mixed with a given volume of gold-labelled anti-αGST IgG using Tris buffered saline, pH 7.4, containing 0.5% (w/v) Tween 20 as diluent.

2. A nitrocellulose membrane strip, pre-coated with anti-αGST IgG, was dipped into the mixture and left in place for up to 5 minutes.

Testing Procedure:

The rapid assay procedure was carried out on the following samples:

Sample No. 1: αGST at 250 ng/ml.

Sample No. 2: Diluent only.

Results:

Sample No. 1: A clear detectable signal was obtained in the assay.

Sample No. 2: No signal was obtained when diluent only was tested in the assay.

Principle of the Technique and Interpretation of Results for Examples 2 and 3

Gold-labelled anti-αGST IgG migrates up the membrane. If αGST is present in the mixture then the gold-labelled IgG/αGST complex binds to the immobilised anti-αGST IgG on the membrane to form a pink-red line (precipitate). If no αGST is present in the mixture then the gold-labelled anti-αGST IgG chromatographs to the top of the membrane and no line (precipitate) is observed.

The technique is also illustrated with reference to FIG. 1. In FIG. 1 a nitrocellulose membrane strip is indicated generally at 10 and is shown dipping into a sample of biological fluid in a receptacle 11 containing a gold-labelled anti-αGST IgG. A band (1–3 mm) of immobilised anti-αGST IgG is shown in dotted outline at 12. Direction of flow of the sample on the nitrocellulose membrane 10 is indicated by the arrow. The gold-labelled anti-αGST IgG binds αGST, if present, and migrates up the membrane and is captured by the immobilised IgG at 12. Nitrocellulose membrane 10 is left in contact with the sample for 3–5 minutes and is then removed as depicted by strips A and B. If αGST is present (positive result) a pink-red line (precipitin line) is observed as shown on strip A. If no αGST is present (negative result) no pink-red line forms at 12 as shown on strip B. The arrangement in FIG. 1 is purely illustrative and in a commercial embodiment the gold-labelled anti-αGST would generally be provided (as a mobile phase) on the nitrocellulose membrane adjacent the sample application end 13.

The particular advantages of this rapid assay format will be apparent, since only a single step is involved in the entire procedure. However, it will be appreciated that the rapid assay format according to the invention represents significant improvement over conventional microtitre plated-based immunoassays.

EXAMPLE 4

αGST Particle-Based Assay

1. Anti-αGST IgG (murine monoclonal; 1 mg/ml in PBS) was immobilised onto nitrocellulose membrane strips (0.5×4 cm) at an area approximately 1 cm from the top of the strip.

2. The strips were blocked by incubation for 30 minutes at room temperature in a solution of 2% (w/v) non-fat milk and 2% (w/v) polyvinylpyrrolidone in Tris buffered saline, pH 7.4, containing 0.5% (w/v) Tween 20.

3. The strips were rinsed with distilled water, and dried for 1 hour at room temperature.

4. Anti-αGST antibodies were labelled with gold particles (40 nm diameter) by a contract manufacturer supplied with the antibody, and were stored in 0.1% (w/v) sodium azide in 2 mM sodium tetraborate at pH 7.2 as diluent.

5. Gold-labelled anti-αGST antibodies were applied to the nitrocellulose membrane strips at an area approximately 3 cm from the top of the strip. Prior to application of the gold-labelled antibodies a sublayer of 30% (w/v) sucrose in distilled water was applied to this area of the strip.
Assay Procedure:

1. αGST containing samples were applied to the nitrocellulose membrane strips.
Testing Procedure:

The rapid assay procedure was carried out on the following samples:

Sample No. 1: αGST at 250 ng/ml, using Tris buffered saline, pH 7.4, containing 0.5% (w/v) Tween 20 as diluent.

Sample No. 2: αGST at 25 ng/ml, using Tris buffered saline, pH 7.4, containing 0.5% (w/v) Tween 20 as diluent.

Sample No. 3: Diluent only.

Sample No. 4: Two diluted perfusate samples with known αGST concentrations (a) 6716 and (b) 29295 ng/ml, before 1/20 dilution.

Sample No. 5: Three diluted serum samples with known αGST concentrations (a) 26.62 (b) 119.34 and (c) 251.86 ng/ml, before 1/20 dilution.

Sample No. 6: Three diluted bile samples with known αGST concentrations (a) 7.26 (b) 31.93 and (c) 68.12 ng/ml, before 1/20 dilution.

Sample No. 7: A diluted urine sample with a known αGST concentration of 88.07 ng/ml before 1/20 dilution.
Results:

Sample No. 1: A clear detectable signal was obtained in the assay.

Sample No. 2: A clear detectable signal was obtained in the assay.

Sample No. 3: No signal was obtained when diluent only was tested in the assay.

Sample No. 4: αGST present in both perfusate samples was detected.

Sample No. 5: No signal was obtained when the serum sample containing 26.62 ng/ml αGST (before 1/20 dilution) was tested, indicating that the assay does not detect αGST at levels corresponding to normal serum levels. αGST present in the samples containing 119.34 and 251.86 ng/ml αGST (before 1/20 dilution) was detected.

Sample No. 6: No signal was obtained when the bile samples containing 7.26 and 31.93 ng/ml αGST (before 1/20 dilution) were tested, indicating that the assay does not detect αGST at these levels.

αGST present in the sample containing 68.12 ng/ml αGST (before 1/20 dilution) was detected.

Sample No. 7 αGST present in the urine sample was detected.

Principle of the Technique and Interpretation of Results for Example 4

As the test sample migrates along the nitrocellulose membrane strip it mixes with the gold-labelled anti-αGST antibodies on the strip. If αGST is present in the sample, the labelled anti-αGST antibodies bind to the αGST forming an antibody-antigen complex. This complex migrates along the strip and binds to the anti-αGST IgG immobilised onto the strip, and produces a pink-red line. If no αGST is present in the sample the labelled anti-αGST antibodies migrate to the top of the strip, and no line is observed.

The technique is also illustrated schematically with reference to FIG. 2. A nitrocellulose membrane strip is shown generally at 20; near its end 21 is an area 22 bearing gold-labelled anti-αGST antibodies. Upstream of the strip 20 is an area 23 with immobilised anti-αGST IgG in the form of a band. Sample is applied to the end 21, and migrates along the strip towards the end 24. In so doing, the sample mixes with the gold-labelled anti-αGST antibodies at 22 and αGST, if present in the sample, binds to the gold-labelled antibodies forming an antibody-antigen complex. This complex binds to the anti-αGST IgG immobilised at 23 and produces a pink-red line. If no αGST is present in the sample, no pink-red line forms at 23.

EXAMPLE 5

πGST Particle-Based Assay

1. Anti-πGST IgG (murine monoclonal; 0.6 mg/ml in PBS) was spotted onto nitrocellulose membrane strips (1 μl/dot=0.6 μg). No blocking step was included in the membrane preparation, however the inclusion of such a procedure may aid strip stability and reduce non-specific binding.

2. Anti-πGST antibodies (rabbit polyclonal) were labelled with gold particles (40 nm diameter) by a contract manufacturer supplied with the antibody and were stored in 0.1% (w/v) sodium azide in 2 mM sodium tetraborate at pH 7.2 as diluent.

Assay procedure

1. πGST-containing samples (10 μl each @ 1–500 μg/ml) were mixed with a given volume (50 μl) of gold-labelled anti-πGST IgG and 140 μl of the following diluent:

1% (w/v) bovine serum albumin

1% (w/v) TWEEN-20 in PBS, pH 7.2 and were tested as hereinafter described.

2. The nitrocellulose membrane, pre-coated with anti-πGST IgG (0.6 μg/dot), was dipped into the mixture and left in place for up to 3–15 minutes.

Testing Procedure

The rapid assay procedure was carried out on the following samples:

Sample Nos. 1–4: containing πGST in buffer only;

Sample No. 5: containing buffer only; and

Sample Nos. 6–15: urine, bile and plasma containing πGST, as set forth in Table 1.

Sample Nos. 7 and 8 (urine) and 12 and 13 (plasma) were spiked with purified πGST. However the bile samples contained inate πGST.

TABLE 1

| Sample No. | | Initial conc. (ng/ml) | Final conc. (ng/ml) | Amount Present (ng) |
|---|---|---|---|---|
| 1 | | 500,000 | 25,000 | 5000 |
| 2 | | 50,000 | 2,500 | 500 |
| 3 | | 5,000 | 250 | 50 |
| 4 | | 1,000 | 50 | 10 |
| 5 | | 0 | 0 | 0 |
| 6 | (Urine) | 30 | 1.5 | 0.3 |
| 7 | (Urine) | 1000 | 50 | 10 |
| 8 | (Urine) | 5000 | 250 | 50 |
| 9 | (Bile) | 150 | 7.5 | 1.5 |
| 10 | (Bile) | >5000 | >250 | >50 |
| 11 | (Bile) | 3730 | 186.5 | 37.2 |
| 12 | (Plasma) | 1000 | 50 | 10 |
| 13 | (Plasma) | 5000 | 250 | 50 |
| 14 | (Plasma)* | 1000 | 250 | 50 |
| 15 | (Plasma) | 120 | 6 | 1.2 |

*(50 μl sample + 50 μl gold-labelled anti-πGST IgG and 100 μl diluent)

TABLE 2

Results
The results are set forth in Table 2

| Sample No. | Result |
|---|---|
| Sample No. 1 | YES |
| Sample No. 2 | YES |
| Sample No. 3 | YES |
| Sample No. 4 | YES |
| Sample No. 5 | NO |
| Sample No. 6 | NO |
| Sample No. 7 | YES |
| Sample No. 8 | YES |
| Sample No. 9 | NO |
| Sample No. 10 | YES |
| Sample No. 11 | YES |
| Sample No. 12 | YES |
| Sample No. 13 | YES |
| Sample No. 14 | YES |
| Sample No. 15 | NO |

It can be seen from the above results that πGST is detectable in urine, bile and plasma samples. The sensitivity of the assay appears to be around 50 ng/ml but it is likely that assay optinisation could improve this level of sensitivity. However, this level of πGST has already been observed in biological samples (e.g. bile and tissue perfusion media).

A monoclonal-polyclonal antibody sandwich was found to be necessary for πGST detection by this assay format. However it is possible that if a polyclonal antibody of sufficient sensitivity was identified that this IgG would function in the assay (as in the case of rapid assay format described hereinabove for αGST). Alternatively, a monoclonal/monoclonal type assay may also give sufficient sensitivity.

EXAMPLE 6

πGST Particle-Based Assay

1. Anti-πGST IgG (murine monoclonal; 0.6 mg/ml in PBS) was immobilised onto nitrocellulose membrane strips (0.5×4 cm)

2. The strips were blocked by incubation for 30 minutes at room temperature in a solution of 2% (w/v) non-fat milk and 2% (w/v) polyvinylpyrrolidone in Tris buffered saline, pH 7.4, containing 0.5% (w/v) Tween 20.

3. The strips were rinsed with distilled water, and dried for 1 hour at room temperature.

4. Anti-πGST antibodies were labelled with gold particles (40 nm diameter) by a contract manufacturer supplied with the antibody, and were stored in 0.1% (w/v) sodium azide in 2 mM sodium tetraborate at pH 7.2 as diluent.

Assay Procedure:

1. πGST containing samples were mixed with a given volume of gold-labelled anti-πGST IgG using Tris buffered saline, pH 7.4, containing 0.5% (w/v) Tween 20 as diluent.

2. A nitrocellulose membrane strip, pre-coated with anti-πGST IgG, was dipped into the mixture and left in place for up to 30 minutes.

Testing Procedure:

The rapid assay procedure was carried out on the following samples:

Sample No. 1: πGST at 250 ng/ml.

Sample No. 2: Diluent only.

Results:

Sample No. 1: A clear detectable signal was obtained in the assay.

Sample No. 2: No signal was obtained when diluent only was tested in the assay.

Principle of the Technique and Interpretation of Results for Examples 5 and 6

Gold labelled anti-πGST IgG migrates up the membrane. If πGST is present in the mixture then the gold-labelled IgG/πGST complex binds to the immobilised anti πGST monoclonal IgG on the membrane to form a pink-red line (precipitate). If no πGST is present in the mixture then the gold-labelled anti-πGST IgG chromatographs to the top of the membrane and no line (precipitate) is observed.

It will be appreciated that this assay format also represents a significant step forward when compared to conventional microtitre plate (or membrane)-based assays, since only a single step is involved in the entire procedure.

EXAMPLE 7

πGST Particle-Based Assay

1. Anti-πGST IgG (murine monoclonal; 0.6 mg/ml in PBS) was immobilised onto nitrocellulose membrane strips (0.5×4 cm) at an area approximately 1 cm from the top of the strip.

2. The strips were blocked by incubation for 30 minutes at room temperature in a solution of 2% (w/v) non-fat milk and 2% (w/v) polyvinylpyrrolidone in Tris buffered saline, pH 7.4, containing 0.5% (w/v) Tween 20.

3. The strips were rinsed with distilled water, and dried for 1 hour at room temperature.

4. Anti-πGST antibodies were labelled with gold particles (40 nm diameter) by a contract manufacturer supplied with the antibody, and were stored in 0.1% (w/v) sodium azide in 2 mM sodium tetraborate at pH 7.2 as diluent.

5. Gold-labelled anti-πGST antibodies were applied to the nitrocellulose membrane strips at an area approximately 3 cm from the top of the strip. Prior to application of the gold-labelled antibodies a sublayer of 30% (w/v) sucrose in distilled water was applied to this area of the strip.

Assay Procedure:

1. πGST containing samples were applied to the nitrocellulose membrane strips.

Testing Procedure:

The rapid assay procedure was carried out on the following samples:

Sample No. 1: πGST at 250 ng/ml, using Tris buffered saline, pH 7.4, containing 0.5% (w/v) Tween 20 as diluent.

Sample No. 2: πGST at 25 ng/ml, using Tris buffered saline, pH 7.4, containing 0.5% (w/v) Tween 20 as diluent.

Sample No. 3: Diluent only.

Results:

Sample No. 1 and 2: A clear detectable signal was obtained in the assay for both samples, and the signal intensity was proportional to the πGST concentration.

Sample No. 3: No signal was obtained when diluent only was tested in the assay.

Principle of the Technique and Interpretation of Results for Example 7

As the test sample migrates along the nitrocellulose membrane strip it mixes with the gold-labelled anti-πGST antibodies on the strip. If πGST is present in the sample, the labelled anti-πGST antibodies bind to the πGST forming an antibody-antigen complex. This complex binds to the anti-πGST IgG immobilised onto the strip, and produces a pink-red line. If no πGST is present in the sample the labelled anti-πGST antibodies migrate to the top of the strip, and no line is observed. Thus, the technique corresponds to that described in relation to Example 4 and as illustrated in FIG. 2.

What is claimed is:

1. A method for the rapid assessment of organ status in a subject based on the detection of one or more isoenzymes of gluthatione S-transferase (GST) in biological fluids, which method comprises contacting a particle-labelled anti-GST antibody specific for said isoenzyme with a sample of a biological fluid suspected of containing said isoenzyme, said antibody having a sensitivity sufficient to detect at least a picomolar amount of said isoenzyme, and capturing the particle-labelled antibody-isoenzyme complex on an immobilised capture antibody to generate a visually detectable signal, wherein a presence or absence of said isoenzyme, as detected by a visual signal generated without an amplification step, indicates organ status.

2. A method according to claim 1, wherein the GST is alpha GST (αGST).

3. A method according to claim 1, wherein the GST is piGST (πGST).

4. A method according to any one of claims 1–3, wherein the anti-GST antibody is polyclonal antibody.

5. A method according to claim 4, wherein the anti-GST antibody is anti-αGST antibody which has an affinity to detect α-GST concentrations of as low as 6.5 ng/ml.

6. A method according to claim 1, wherein the capture antibody is bound to a nitrocellulose membrane.

7. A method according to claim 6, wherein non-specific binding sites present on the nitrocellulose membrane are blocked.

8. A method according to claim 1, wherein the biological fluid is diluted.

9. A method according to claim 1, wherein the biological fluid is selected from bile, plasma, serum and urine.

10. A method according to claim 1, wherein the biological fluid is a perfusate and the method is used to evaluate an organ prior to transplantation or ex vivo experimentation.

11. A method according to claim 1, wherein said particles are gold particles having an average diameter in the range 15–40 nm.

12. A method according to claim 1, wherein the antibody sensitivity is sufficient to detect amounts as low as 6.5 ng/ml of said isoenzyme.

13. A method according to claim 1, wherein the organ in which damage is to be detected is a kidney or a liver.

14. A kit for carrying out a method according to claim 1, which contains mobile particle-labelled anti-GST antibody which is specific for a GST isoenzyme, wherein said particle-labelled antibody is capable of generating a visually detectable signal without amplification; and capture antibody, which is specific for a GST isoenzyme-labelled antibody complex, immobilized on a solid phase.

* * * * *